US008029523B2

(12) United States Patent
Wallis et al.

(10) Patent No.: US 8,029,523 B2
(45) Date of Patent: Oct. 4, 2011

(54) MAXILLARY BONE CUTTING SYSTEM, KIT, AND METHOD OF USING THE SAME

(75) Inventors: Antonio Jose Gordils Wallis, Mochi Caracas (VE); Ronald G. Litke, Jr., Danbury, CT (US); Ronald T. Callahan, II, Naugatuck, CT (US); Edward Riemer, Seymour, CT (US); Ernesto Hernandez, Weston, FL (US)

(73) Assignee: Innovative Implant Technology, LLC, Weston, FL (US)

( * ) Notice: Subject to any disclaimer, the term of this patent is extended or adjusted under 35 U.S.C. 154(b) by 1057 days.

(21) Appl. No.: 11/853,082

(22) Filed: Sep. 11, 2007

(65) Prior Publication Data

US 2008/0243123 A1 Oct. 2, 2008

Related U.S. Application Data

(60) Provisional application No. 60/909,240, filed on Mar. 30, 2007.

(51) Int. Cl.
*A61B 17/16* (2006.01)
(52) U.S. Cl. ............ 606/173; 408/132; 81/58.3; 81/457
(58) Field of Classification Search .................. 606/79, 606/80, 81, 82, 83, 84, 96, 167, 172, 173, 606/180; 433/75, 76, 165; 408/7, 12, 14, 408/15, 97, 118, 121, 132, 141, 142; 81/28, 81/58, 58.3, 457
See application file for complete search history.

(56) References Cited

U.S. PATENT DOCUMENTS 2,813,280 A * 11/1957 Huffman ..................... 408/10

| | | |
|---|---|---|
| 4,456,010 A | 6/1984 | Reimels et al. |
| 4,600,006 A | 7/1986 | Baker |
| 4,699,550 A | 10/1987 | Baker |

(Continued)

FOREIGN PATENT DOCUMENTS

DE 3503098 C2 3/1994

(Continued)

OTHER PUBLICATIONS

Codman Craniotomy Kit product description page, Johnson & Johnson Gateway, available at http://www.jnjgateway.com/home.jhtml?loc=CAENG&page=viewContent&contentId=09008b9880b49.

(Continued)

*Primary Examiner* — Thomas C Barrett
*Assistant Examiner* — Christian Sevilla
(74) *Attorney, Agent, or Firm* — Gordon & Jacobson, PC

(57) ABSTRACT

A device includes a tubular element, and a cutter spring-biased relative to the tubular element. In an unloaded configuration the cutter is displaced relative to the tubular element by a displacement distance, and when the cutter is in a loaded configuration the displacement distance is reduced. A first structure is longitudinally fixed relative to the cutter and rotationally engaged relative to the tubular element. A length of the first structure extends proximally in the unloaded configuration. A second structure is longitudinally displaceable relative to the first structure. In the loaded configuration, a driver engages and rotates both the first and second structures, and thus the tubular element and cutter together. Once the cutter breaks through the bone, the cutter spring-biased into the unloaded configuration, resulting in disengagement of the first structure from the driver to prevent rotation of either the tubular element or the cutter.

43 Claims, 13 Drawing Sheets

U.S. PATENT DOCUMENTS

| | | |
|---|---|---|
| 4,803,982 A | 2/1989 | Baker |
| 4,884,571 A | 12/1989 | Baker |
| 4,951,690 A | 8/1990 | Baker |
| 5,007,911 A | 4/1991 | Baker |
| 5,135,532 A | 8/1992 | Baker |
| 5,382,250 A | 1/1995 | Kraus |
| 5,653,712 A | 8/1997 | Stern |
| 5,658,305 A | 8/1997 | Baker |
| 5,665,097 A | 9/1997 | Baker et al. |
| 6,908,469 B2 | 6/2005 | Sellers et al. |
| 2006/0084034 A1 | 4/2006 | Hochman |

FOREIGN PATENT DOCUMENTS

| | | |
|---|---|---|
| DE | 3624860 C2 | 10/1994 |
| DE | 3890886 C2 | 1/1999 |
| WO | WO89/03198 | 4/1989 |

OTHER PUBLICATIONS

Our Latest Masterpiece Acra-Cut Smart Drill product description (Model 200-500), 2003 Acra-Cut, Inc.

\* cited by examiner

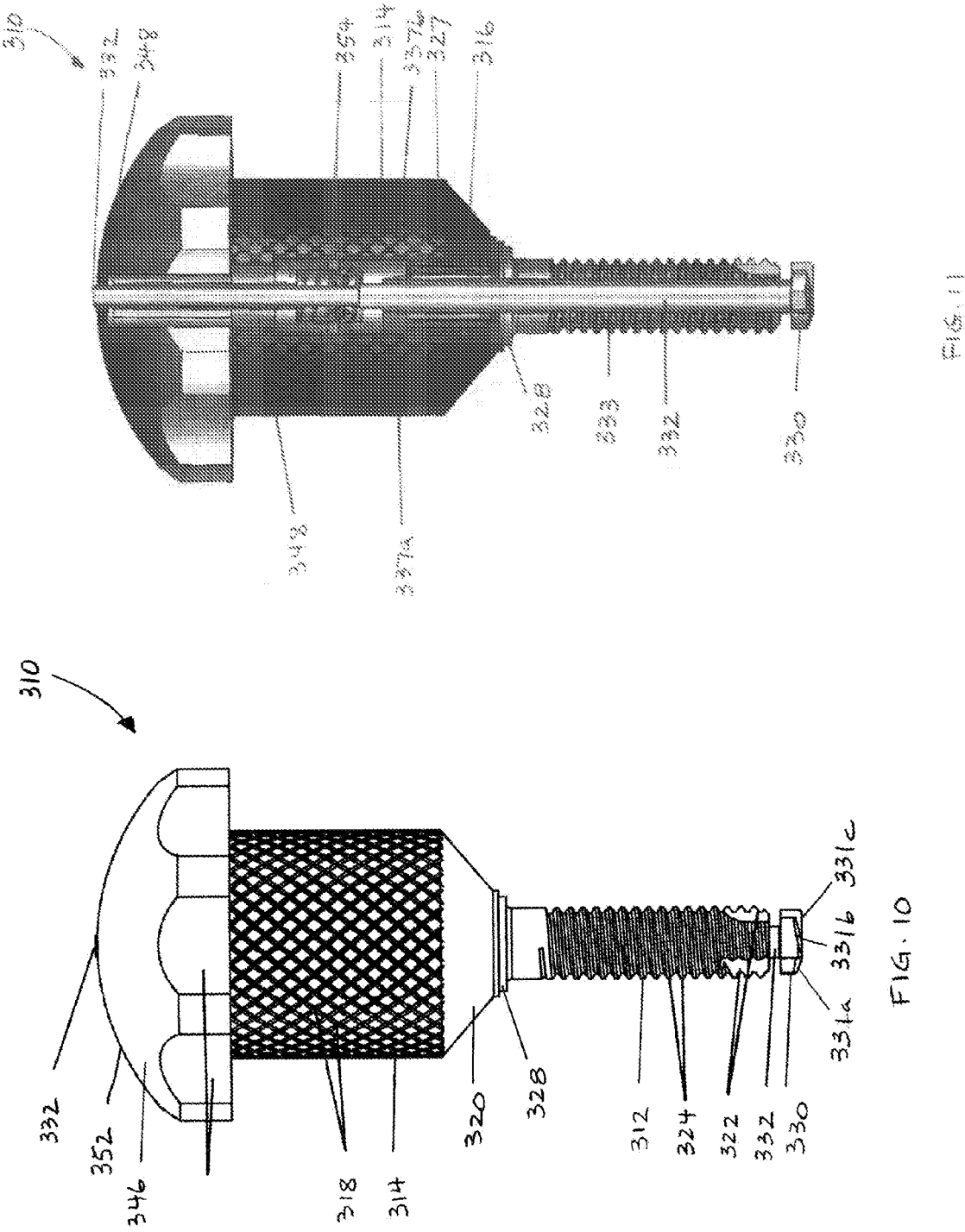

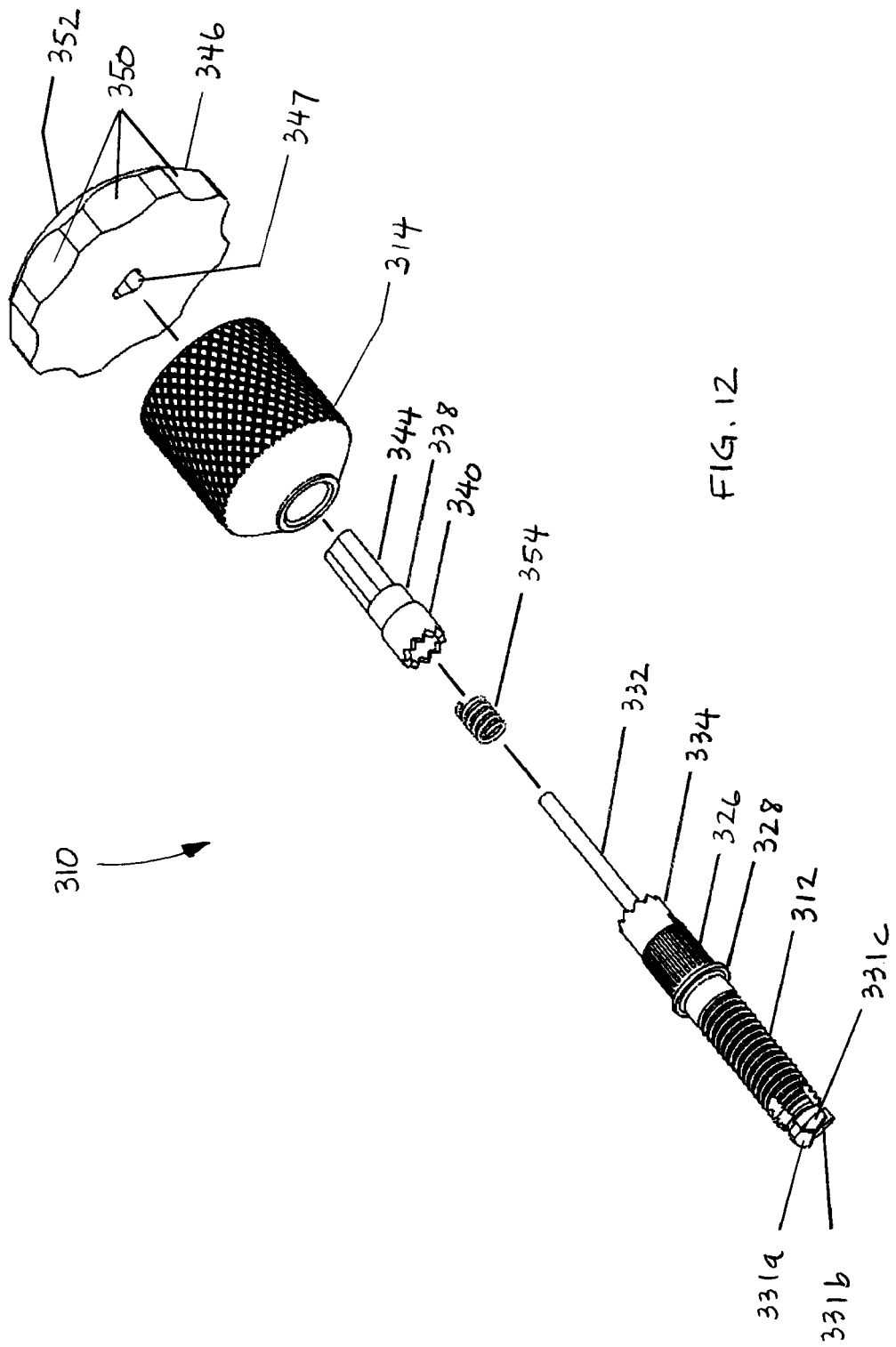

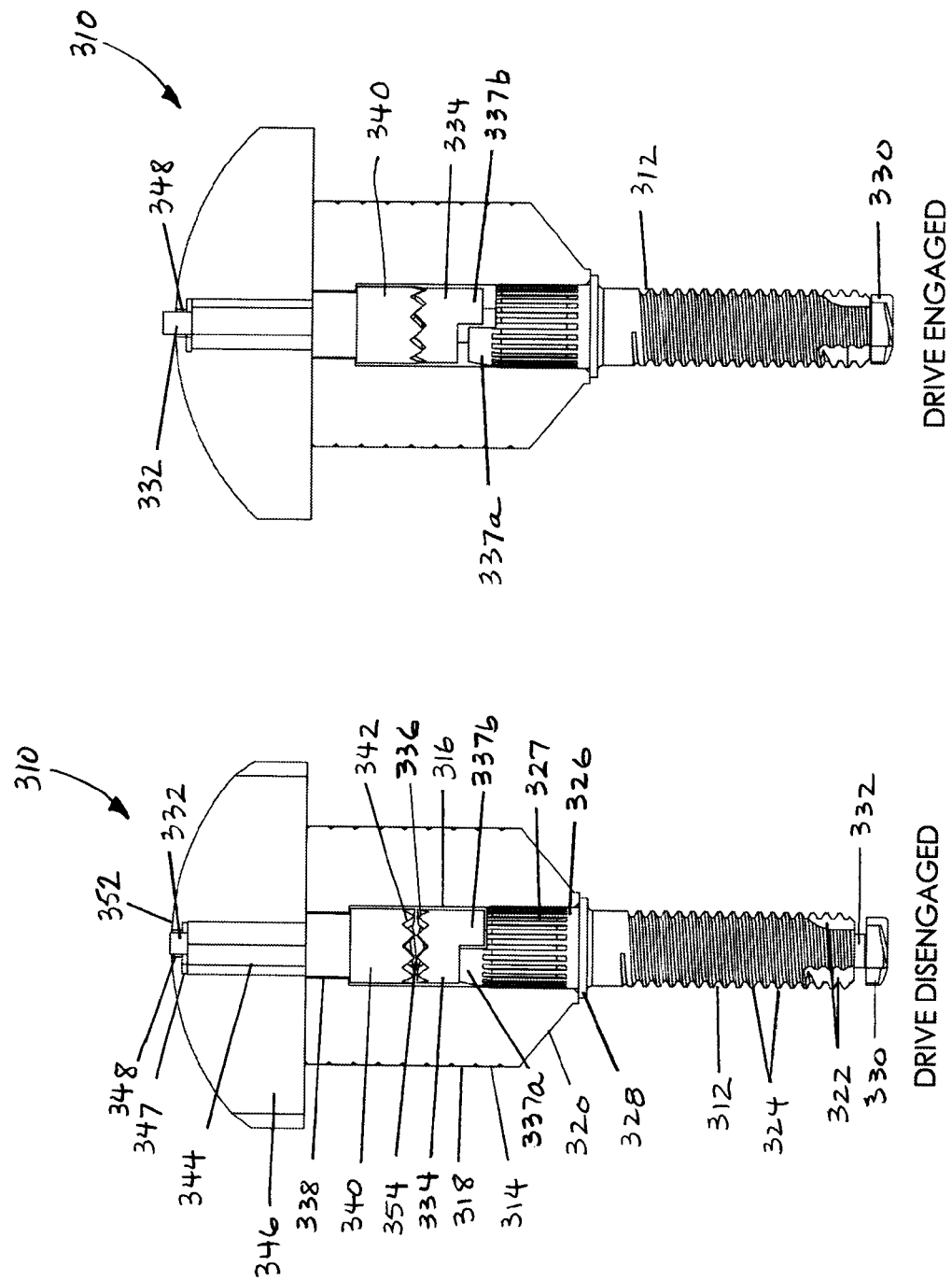

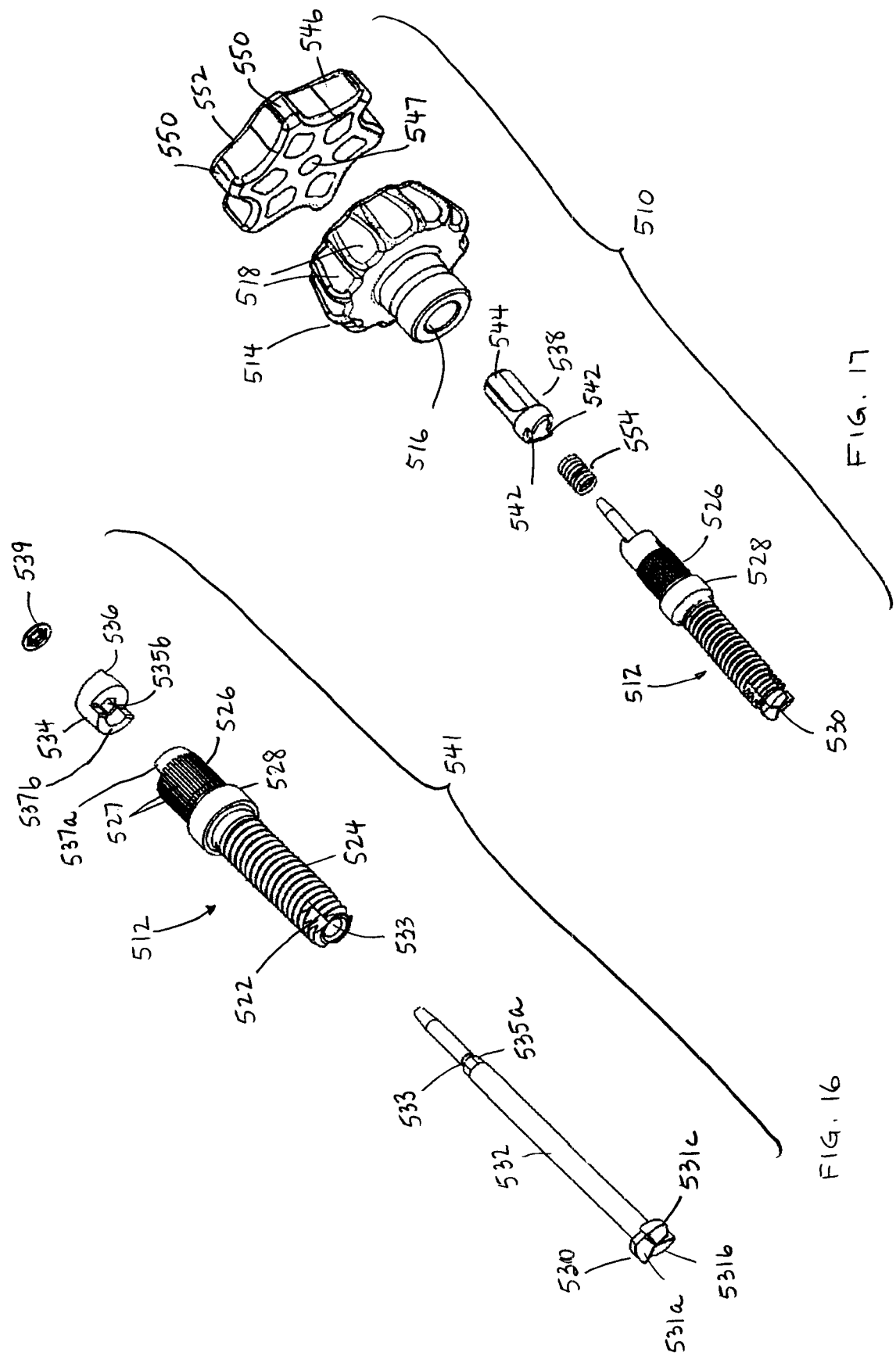

MAXILLARY BONE CUTTING SYSTEM, KIT, AND METHOD OF USING THE SAME

CROSS-REFERENCE TO RELATED APPLICATIONS

This applicant claims the benefit of U.S. Ser. No. 60/909,240, filed Mar. 30, 2007, which is hereby incorporated by reference herein in its entirety.

BACKGROUND OF THE INVENTION

1. Field of the Invention

This invention relates broadly to dental implants. More particularly, this invention relates to tools for the removal of maxillary bone for access to, dissection of and elevation of the subantral membrane of the maxillary sinus for osseous regeneration in order to increase the bony support structure for a dental implant, and for receiving a dental implant.

2. State of the Art

Dental implants have been used in dentistry for about twenty years. They offer a tremendous benefit to patients by allowing the replacement of missing teeth. The success of a dental implant is based on a variety of factors including: surgical technique, health of the patient, operator skill and, to a significant part, sufficient bone for the placement and integration of the dental implant. To that end, dental implants are commonly used in the anterior lower jaw, as this region provides sufficient bone quantity, quality and strength to support and hold the dental implant. However, the replacement of the maxillary teeth have presented a considerable challenge because after the loss of maxillary teeth the quality and quantity of the remaining supporting bone may be insufficient to properly and reliably support the dental implant.

More particularly, the maxillary complex is a three-dimensional bone structure composed of alveolar bone and basal bone. The maxillary teeth, and more specifically the teeth roots, are imbedded in the alveolar bone. The top of the maxillary complex forms the floor of the maxillary sinus and is covered by a thin diaphanous membrane known as the subantral or Schneiderian membrane (referred to herein as the "subantral membrane"). Once a tooth is removed from the maxillary complex, the surrounding alveolar bone is frequently resorbed because of the lack of physical stimulation and support of the teeth. This leads to a loss of bone mass and a corresponding reduction in the effective height and thickness of the bone of the maxillary complex, which if not remedied limits the potential use of the dental implant.

To overcome the deficiency of insufficient vertical bone mass of the maxillary complex, several surgical techniques have been developed to increase available bone mass for the placement of dental implants. These techniques augment the bone deficient region with a filler or regenerative material made of natural and/or artificial (synthetic) materials (collectively, 'bone graft material'). Such material is placed on the roof of the maxillary structure under the subantral membrane so that it does not interfere with the function of the maxillary sinus. Collectively, these procedures are known within the dental profession as "sinus elevation procedures" with the goal of increasing the vertical height available for placement of dental implants. What makes these techniques unique from other techniques, such as distraction osteogenesis, is that the bone is increased within a body cavity, i.e., the maxillary sinus cavity.

Bone augmentation of the maxillary sinus requires careful bone removal and delicate dissection of the subantral membrane from the floor of the sinus. If the membrane is not properly dissected from the bone, bone augmentation may not occur, or may not be sufficient. Unintentional perforation of the subantral membrane may also lead to undesirable short and long-term consequences. If the perforation is large, for example, several millimeters in diameter, the surgeon must either abort the procedure or must use some means of removing or containing the bone graft material on the floor of the sinus to encourage new bone growth. Typically, a collagen membrane patch is used to repair the perforation and contain the bone graft material on the floor of the sinus. A lack of integrity of the membrane can also lead to the migration of bone graft materials leading to long-term chronic infections. Therefore, the maintenance of membrane integrity is of utmost importance during the elevation of the membrane to allow placement of bone graft materials with a goal of increasing bone mass in the maxilla.

A commonplace sinus elevation procedure requires a window into the maxillary sinus from a lateral and superior approach to the floor of the sinus. Great care must be taken during the entry to the sinus as it is critical not to perforate the subantral membrane that lines the sinus cavity. Most patients and dental surgeons acknowledge that entrance into the maxillary sinus utilizing a lateral window approach (also known as the Caldwell-Luc procedure) is an invasive procedure. This technique is fraught with many risks and complications because of the limitations of healing potential in the maxillary sinus. In spite of these risks many patients undergo this procedure because of the strong desire to replace missing maxillary teeth with dental implants.

An alternative procedure described by Dr. R. B. Summers approaches the maxillary sinus from the alveolar ridge utilizing solid cylindrical osteotomes. It is a more conservative approach and is less invasive. The technique vertically lifts the subantral membrane from the floor of the maxillary sinus via an infracture of the bony floor. The infracture can be performed using solid cylindrical osteotomes with specific diameters that are vertically advanced toward the maxillary sinus producing a mechanical lifting action on the membrane. Bone graft material is then placed into this space for bone augmentation. The bone graft materials are actually used to raise the subantral membrane. While this technique is safer than the lateral window approach, an overzealous use of an osteotome during the procedure can result in the perforation of the subantral membrane with disadvantages discussed above.

Thus, in prior art techniques, advancing a bone cutter through the maxillary bone with insufficient control or feedback may result in tearing or ripping of the subantral membrane. Overcoming these previous limitations in the technique of sinus elevation will reduce infection, bleeding, swelling, pain, suffering and failure when using dental implants in the maxillary sinus.

SUMMARY OF THE INVENTION

It is therefore an object of the invention to provide a device, system, and method for cutting a hole in the maxillary bone for access to the subantral membrane.

It is also an object of the invention to provide a device, system and method for accessing the subantral membrane in a manner that prevents damage to the subantral membrane.

It is further an object of the invention to provide a device, a system and a method for drilling maxillary bone to access the subantral membrane which automatically prevents advancement of the tool once the bone is removed and the subantral membrane is reached.

It is yet another object of the invention to provide tool and methods for accessing the subantral membrane, dissecting the subantral membrane from the maxillary bone without damaging the sinus membrane, and performing a complete sinus elevation procedure.

A device according to the invention is a bone cutter including a tubular element, a piston extending within the tubular element, a bone cutting element at the distal end of the piston, and several tool engagement structures. The tubular element includes a distal end, an outer threaded surface engageable and rotatably advanceable into bone, a proximal end including a recess with a non-circular cross-sectional shape, and an inner bore extending between the proximal and distal ends. The piston has proximal and distal ends, and is longitudinally displaceable within the inner bore of the tubular member. The piston is spring-biased relative to the tubular member such that the bone cutting element extends beyond the distal end of the tubular element by a first displacement distance in an unloaded configuration. A first non-circular external tool engagement structure is longitudinally fixed relative to the piston and provided partially within the recess at the proximal end of the tubular element so as to be rotationally engaged relative to the tubular element. In addition, the first tool engagement structure extends proximally a first engagement length from the recess in the unloaded configuration. A second non-circular external tool engagement structure is provided proximally thereof and is longitudinally displaceable relative to the first engagement structure. The second structure includes an external O-ring. The first and second non-circular engagement structures have substantially common diameters.

It is preferred that the proximal end of the tubular element include a third non-circular external tool engagement structure. Initially, a torque applying tool having a socket sized and shaped for rotational engagement at the third tool engagement structure is used to rotate the threaded tubular element into a hole initiated, e.g., with a drill. As the bone cutter is advanced and reaches the closed end of the hole, the cutting element is moved from the unloaded configuration against the spring-bias toward the distal end of the tubular element into a loaded configuration so as to reduce or eliminate the first displacement distance. This causes the first tool engagement structure to extend a second engagement length from the recess greater than the first engagement length.

A second smaller torque applying tool having a socket sized and shaped for rotational engagement at the first and second tool engagement structures is provided. More particularly, the second tool has a distal end sized to abut the proximal end of the tubular element, a socket for engagement of the first and second engagement structures, an upper recess with a diameter larger than the first engagement structure, and an internal circumferential recess. When the second tool is provided over the first and second tool engagement structures, the O-ring of the second tool engagement structure engages within the circumferential recess. In the loaded configuration, the first tool engagement structure extending the second engagement length from the recess allows the second tool to engage and rotate both the first and second tool engagement structures, and thus the tubular element and cutter together.

When the cutting element breaks through the bone just under the subantral membrane, the cutting element is displaced by the spring-bias into the unloaded configuration, slightly lifting the membrane by, at most, the first displacement distance. Such displacement does not cause any damage to the membrane. When the cutting element and piston are moved distally relative to the tubular element, the first tool engagement structure longitudinally fixed relative to the piston is also moved relatively distally. This causes the portion of the first tool engagement structure that extends from the proximal recess of the tubular element to be reduced to the first engagement length such that the proximally extending portion of the first tool engagement structure disengages from the socket and resides within the recess of the second tool. As a result, further rotation of the socket will not cause rotation of either the tubular element or the cutter, and further advancement of the cutter into the maxillary bone is prevented.

The device is then removed from the hole in the maxillary bone by re-engaging the first tool at the third tool engagement structure and rotating the tubular element in a direction opposite from insertion.

Second and third embodiments of a device according to the invention are also provided which can be manually operated without the use of discrete first and second tools. In each such embodiment, the device includes a tap fixed within a tap body. A cutting element is situated at the distal end of the tap on a piston that extends through an axial bore in the tap and is then rotatably fixed to and extends through a first toothed gear. The first toothed gear and the proximal end of the tap are rotatably fixed, but longitudinally displaceable relative to each other.

The device also includes a drive shaft including a second toothed gear that mates with the first toothed gear. The drive shaft also preferably includes a proximal end that is rotationally fixed with a driver knob.

A spring is provided between the first and second toothed gears to bias the gears apart into a unengaged configuration when the device is unloaded. When the cutting element is forced against bone to provide the device in a loaded configuration, the first toothed gear is moved against the bias of the spring to engage the first and second gears with each other.

In operation, the gingiva is opened to reveal the underlying maxillary bone at the location of an intended dental implant. A hole is marked in the bone with a burr, a small pilot hole is preferably drilled to within preferably approximately 1 to 2 mm of the subantral membrane, and a preferably 3.2 mm drill bit is used to enlarge the hole to such diameter also to within preferably approximately 1 to 2 mm of the subantral membrane. The device of either the second or third embodiments of the invention, is then advanced within the drilled hole by manually rotating the tap body. During initial insertion, it is appreciated that the cutting element is unloaded and the drive gears are disengaged. Once the cutting element reaches the end of the drilled hole, the cutting element is forced against the tap, and the first drive gear is longitudinally moved against the bias of the spring to engage the second drive gear. As the gears are now engaged, user rotation of the driver knob causes rotation of the drive shaft which rotates the second gear which is rotationally engaged to the first gear. As the first gear is then rotated, the tap and cutting element are together rotated to effect cutting of bone. Torque is applied to the driver knob to rotate the cutting element until the cutting element reaches the subantral membrane and, under force of the spring, displaces relative to the distal end of the tap and lifts the subantral membrane off the maxillary bone. The tap body is then rotated to remove the device from the hole.

After the hole is cut through the maxillary bone, any suitable instrument(s) and technique(s) are then used to separate and lift the subantral membrane from the floor of the maxillary sinus to define a space for receiving bone graft material that can support an implant. In a preferred embodiment, curettes as described in co-owned U.S. Ser. No. 11/669,449, incorporated by reference in its entirey herein, are used to separate the subantral membrane from the maxillary sinus floor. Once the subantral membrane is separated from the floor of the sinus, a bone packer is used to place and compact bone graft material under the lifted subantral membrane. The gingiva may be closed for healing at this time. Alternatively, a drill corresponding to the anchor of the intened implant is used to drill a hole of corresponding diameter, the implant is placed therein, and the gingiva is closed thereover.

In accord with another aspect of the invention, a kit of tools for performing a sinus elevation procedure is provided. The kit include the bone cutting device, preferably as descrbied above. The kit also includes at least one hand tool, called a currette, to dissect the subantral membrane from the maxillary bone. Preferably two curettes are provided, each of a different dimension and/or flexibility such that the curettes are adapted to separate a different extent of the subantral membrane surrounding the hole defined in the maxillary bone by the bone cutting device. The tools of the kit preferably also include a bone packer to pack bone graft material beneath the dissected membrane. The tools of the kit preferably also include a pilot drill and a 3.2 mm drill for forming the hole in which the bone cutter device can be advanced. All such tools are presented in a sterilized container, preferably in the form of a sealed tray.

Additional features and advantages of the invention will become apparent to those skilled in the art upon reference to the detailed description taken in conjunction with the provided figures.

BRIEF DESCRIPTION OF THE DRAWINGS

FIG. 10 is a side elevation view of another embodiment of a bone cutter device according to the invention, in an unloaded configuration.

FIG. 11 is a partial section view of the bone cutter device of FIG. 10, in an unloaded configuration.

FIG. 12 is an assembly view of the bone cutter device of FIG. 10.

FIG. 13 is a longitudinal section view of the bone cutter device of FIG. 10, in an unloaded configuration.

FIG. 14 is a longitudinal section view of the bone cutter device of FIG. 10, in a loaded configuration.

FIG. 16 is an exploded view of a tap assembly of the cutter device of FIG. 15.

FIG. 17 is an exploded view of the bone cutter of FIG. 15.

DETAILED DESCRIPTION OF THE PREFERRED EMBODIMENTS

Figure 2:
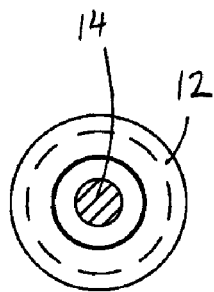
FIG. 2 is a cross-section view across line 2-2 in FIG. 1.
Figure 3:
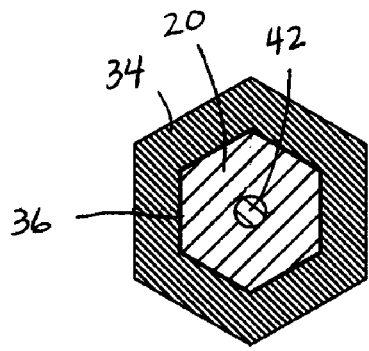
FIG. 3 is a cross-section view across line 3-3 in FIG. 1.
Figure 1:
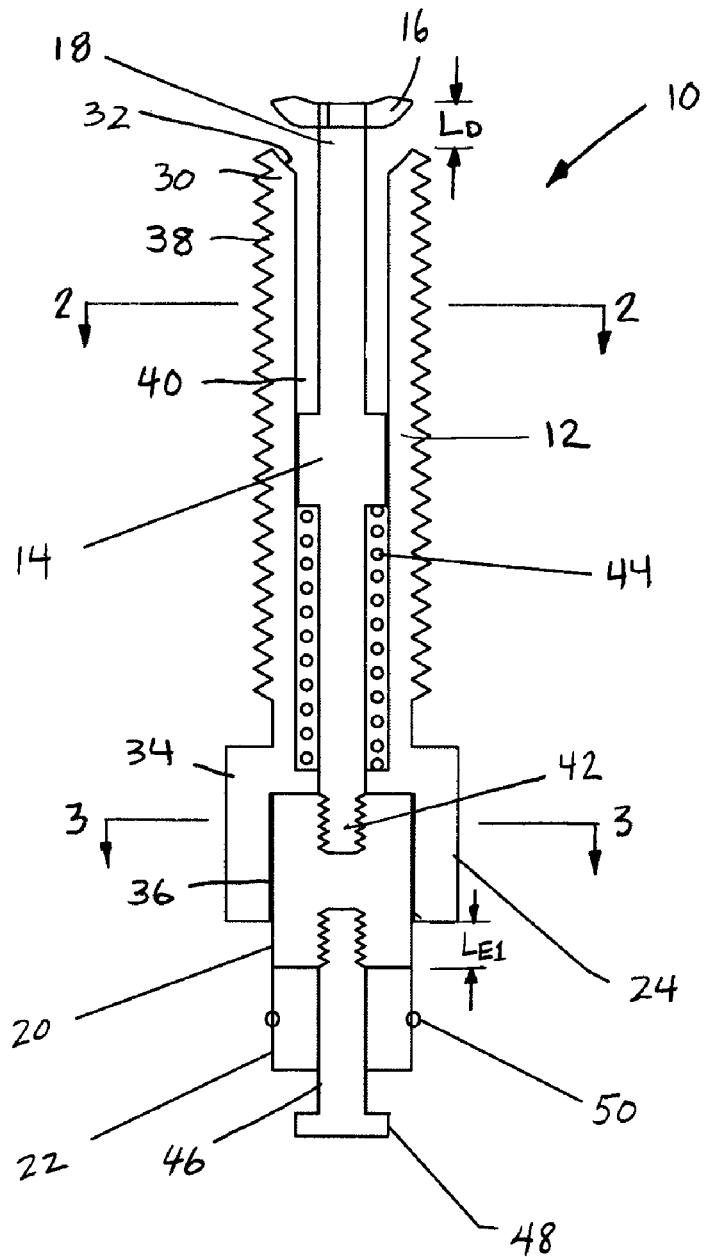
FIG. 1 is a longitudinal section view of a bone cutter device according to the invention, in an unloaded configuration.

Turning now to FIGS. 1 through 3, a bone cutting device 10 for removal of maxillary bone to provide access for dissection of and elevation of the subantral membrane of the maxillary sinus is shown and now described. The device 10 includes a tubular element 12, a piston 14 extending within the tubular element 12, a bone cutting element 16 at the distal end 18 of the piston 14, and several tool engagement structures 20, 22, 24 for engagement by torque applying tools as described in more detail below.

The tubular element 12 includes a distal end 30 defining a recess 32 to partially receive the cutting element when the device 10 is in a loaded configuration (FIG. 5), and a relatively enlarged proximal end 34 including a recess 36 with a non-circular cross-sectional shape. The tubular element 12 also includes a tap (an outer threaded surface) 38 engageable and rotatably advanceable into bone, and an inner bore 40 extending between the proximal and distal ends 34, 30. The piston 14 has a proximal end 42 that extends into proximal recess 36 and distal end 18, and is longitudinally displaceable within the inner bore 40 of the tubular member 12. A coil spring 44 spring-biases the piston 14 relative to the tubular member such that the bone cutting element 16 extends beyond the distal end 30 of the tubular element 12 by a first displacement distance $L_D$ in an unloaded configuration, as shown.

A first non-circular external tool engagement structure 20, e.g., a bolt, is longitudinally fixed to the proximal end 42 of the piston 14 and provided partially within the recess 36 at the proximal end 42 of the tubular element 12 so as to be rotationally engaged relative to the tubular element 12. Recess 36 and structure 20 preferably include corresponding sizes and shapes, and more preferably are hexagonally shaped in cross-section. However, it is not necessary that they have the same shapes; only that the shapes and sizes thereof be rotationally interfering. In addition, the first tool engagement structure 20 extends proximally a first engagement length $L_{E1}$ from the recess 36 in the unloaded configuration.

A pin 46 is longitudinally fixed within the proximal end of the first engagement structure 20 and includes an enlarged free end 48. The second non-circular external tool engagement structure 22, e.g., another bolt, is longitudinally displaceable on the pin 46, between the first engagement structure 20 and the free end 48. The second structure includes an external O-ring 50. The first and second non-circular engagement structures 20, 22 have substantially common diameters (largest cross-sectional dimensions) and preferably a common cross-sectional shape therewith.

It is preferred that the proximal end 34 of the tubular element 12 include the third non-circular external tool engagement structure 24, e.g., a hexagonal cross-sectional shape for engagement by a torque-applying tool, as now described.

Figure 4:
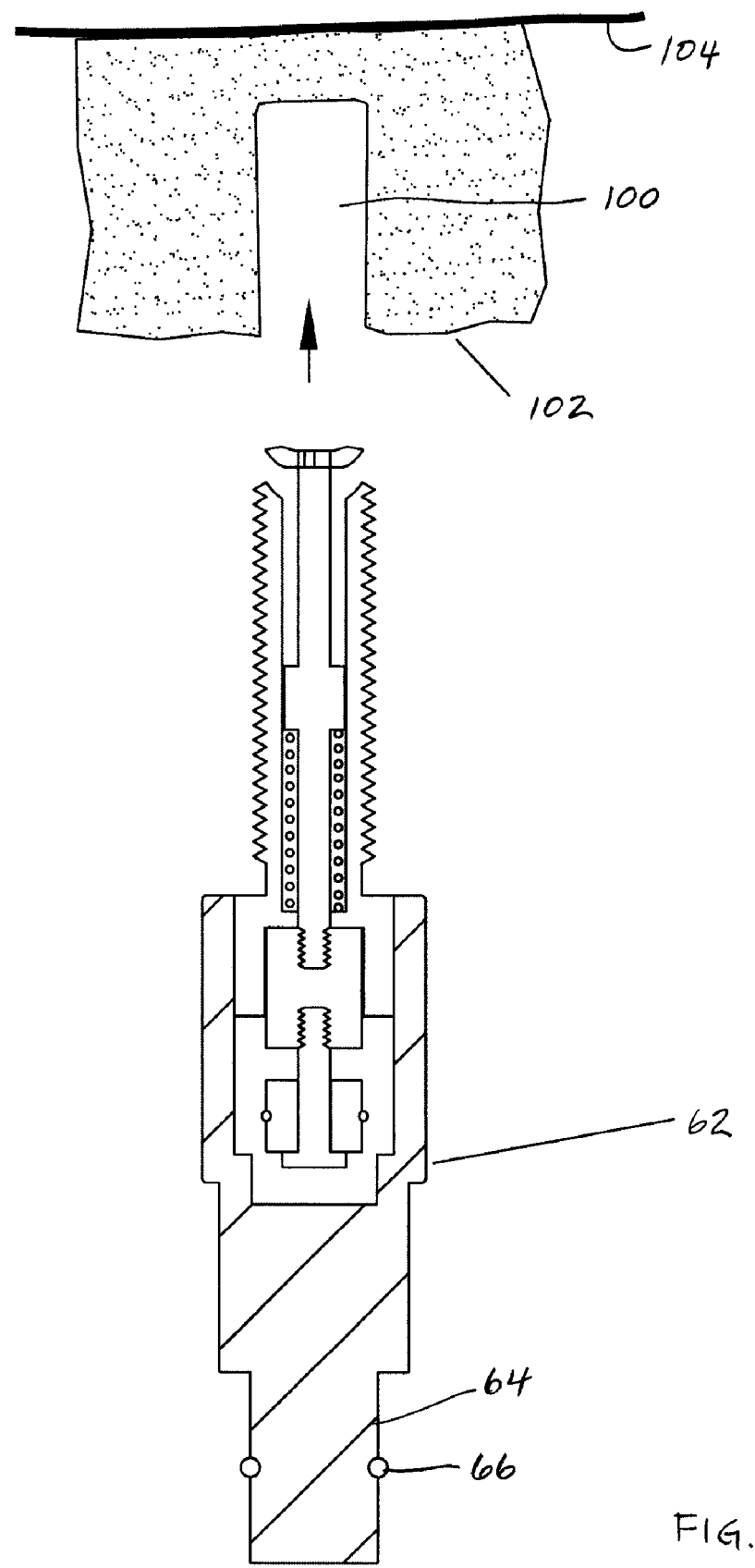
FIG. 4 is a longitudinal section view of a system of the bone cutter device of FIG. 1 engaged by a second tool for advancement into a pilot hole in the maxillary bone.

Referring to FIG. 4, in use, a torque applying tool, e.g., a ratchet socket 60 (wrench not shown) having an opening sized and shaped for rotational engagement at the third tool engagement structure 24 is coupled at structure 24. The socket 60 may be provided in several lengths, e.g., 15 mm and 21 mm, to facilitate access to the maxillary bone in different patients. In addition, the proximal driving end 62 of the socket is preferably provided with an O-ring 64 for secure engagement by an associated wrench. The socket 60 is used to engage the cutting device 10 and rotationally drive the threaded tubular element 12 into a hole 100 in the maxillary bone 102 under the subantral membrane. The hole 100 has preferably previously been initiated with another device, e.g., a drill, as described in more detail below.

Figure 5:
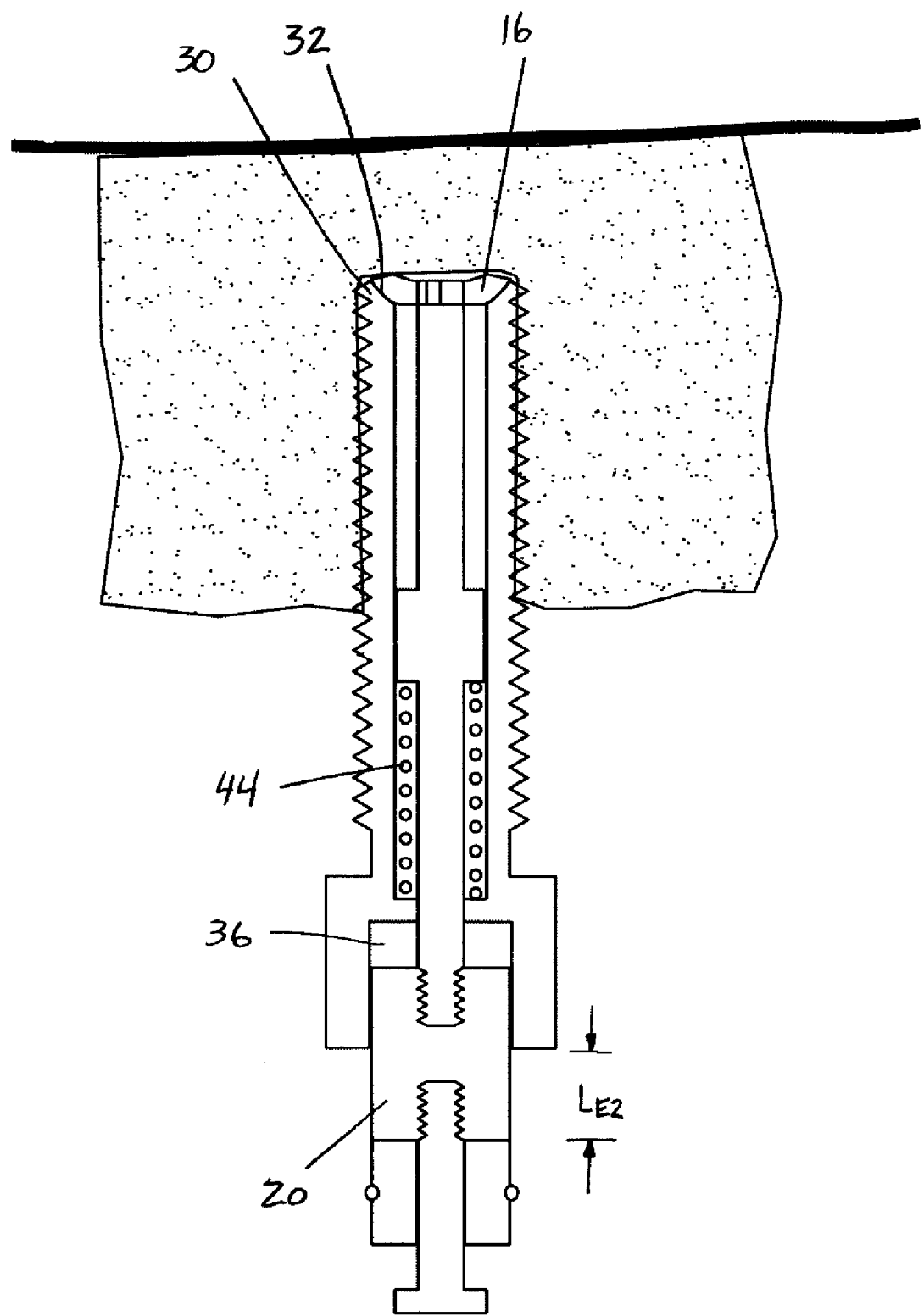
FIG. 5 is a longitudinal section view of the bone cutter device of FIG. 1 provided in the pilot hole in the maxillary bone, in a loaded configuration.

Referring to FIG. 5, as the bone cutter 10 is advanced within the hole 100 and reaches the closed end of the hole, the cutting element 16 is moved from the unloaded configuration against the bias of spring 44 toward the distal end 30 of the tubular element 12 and partially into the recess 32; i.e., into a loaded configuration at least that reduces and preferably substantially or completely eliminates the first displacement distance $L_D$ (FIG. 1). This causes the first tool engagement structure 20 to extend from the recess 36 a second engagement length $L_{E2}$ greater than the first engagement length $L_{E1}$.

Once in the loaded configuration, socket 60 is removed from over engagement structure 24, and a different smaller socket 68 having an opening sized and shaped for rotational engagement of the first and second tool engagement structures 20, 22 is provided. The socket 68 has a distal end 69 sized to abut the proximal end 34 of the tubular element 12, an opening 70 for engagement of the first and second engagement structures 20, 22, an upper recess 72 with a diameter larger than the first engagement structure 20, and an internal circumferential groove 74. When the smaller socket 68 is provided over the first and second tool engagement structures 20, 22, the O-ring 50 of the second tool engagement structure 22 engages within the circumferential groove 74 resisting longitudinal movement therebetween. Alternatively, the O-ring may be provided about the internal circumference of the socket opening and the groove may be provided to the outer circumference to the second tool engagement structure 22. The smaller socket 68 may be provided in several lengths for use on different patients, e.g., 15 mm and 21 mm. In the loaded configuration, the first tool engagement structure 20 extending the second engagement length $L_{E2}$ from the recess 36 allows the smaller socket to engage and rotate both the first and second tool engagement structures 20, 22, and thus the tubular element 12 and cutting element 16. Bone grinding is achieved by rotating the device in the loaded configuration, preferably with a ratchet wrench 76, to effect bone removal and cutting device advancement.

Figure 7:
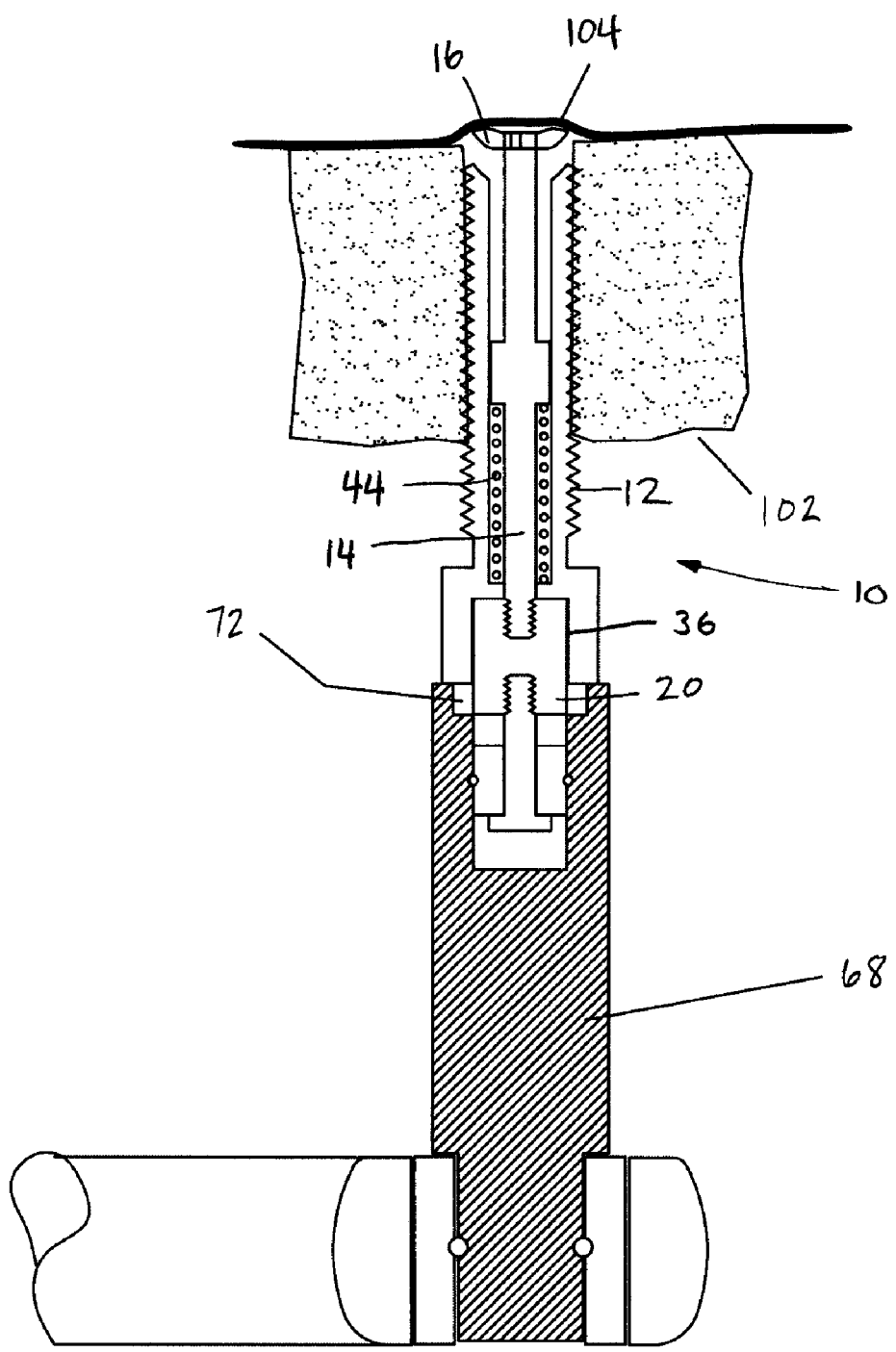
FIG. 7 is a longitudinal section view of a system of the bone cutter device of FIG. 1 engaged by the first tool for bone cutting and advancement into a hole in the maxillary bone, the cutting element breaking through the maxillary bone and lifting the subantral membrane and thus being displaced into the unloaded configuration.

Referring to FIG. 7, once the cutting element 16 breaks through the bone 102 just under the subantral membrane 104, the cutting element is displaced by the spring 44 into the unloaded configuration, slightly lifting the subantral membrane 104 by, at most, the first displacement distance $L_D$. Such displacement is not great enough to cause perforation or any damage to the membrane. Moreover, the slight lifting of the membrane facilitates subsequent 'lifting' procedures to prepare the membrane for receiving bone graft materials for implant support. When the cutting element 16 and piston 14 are moved distally relative to the tubular element 12, the first tool engagement structure 20 longitudinally fixed relative to the piston 14 is also moved relatively distally. This causes the portion of the first tool engagement structure 20 that extends from the proximal recess 36 of the tubular element 12 to be reduced to the first engagement length $L_{E1}$ such that the proximally extending portion of the first tool engagement structure 20 disengages from the small socket and resides within the upper recess 72 of the second socket 68. As a result, further rotation of the cutter device socket 68 will not cause rotation of either the tubular element 12 or the cutting element 16. In fact, the socket 68 is automatically disengaged from further applying torque to any rotationally fixed portion of the cutter device 10. Thus, further advancement of the cutter device 10 into the maxillary bone 102 is automatically prevented.

It is noted that the second tool engagement structure 22 remains stably coupled to the socket 68 even after disengagement of the socket from the first tool engagement structure. The first and second tool engagement structures 20, 22 are longitudinally displaced relative to each other on pin 48 and rotatably coupled relative to each other.

Figure 8:
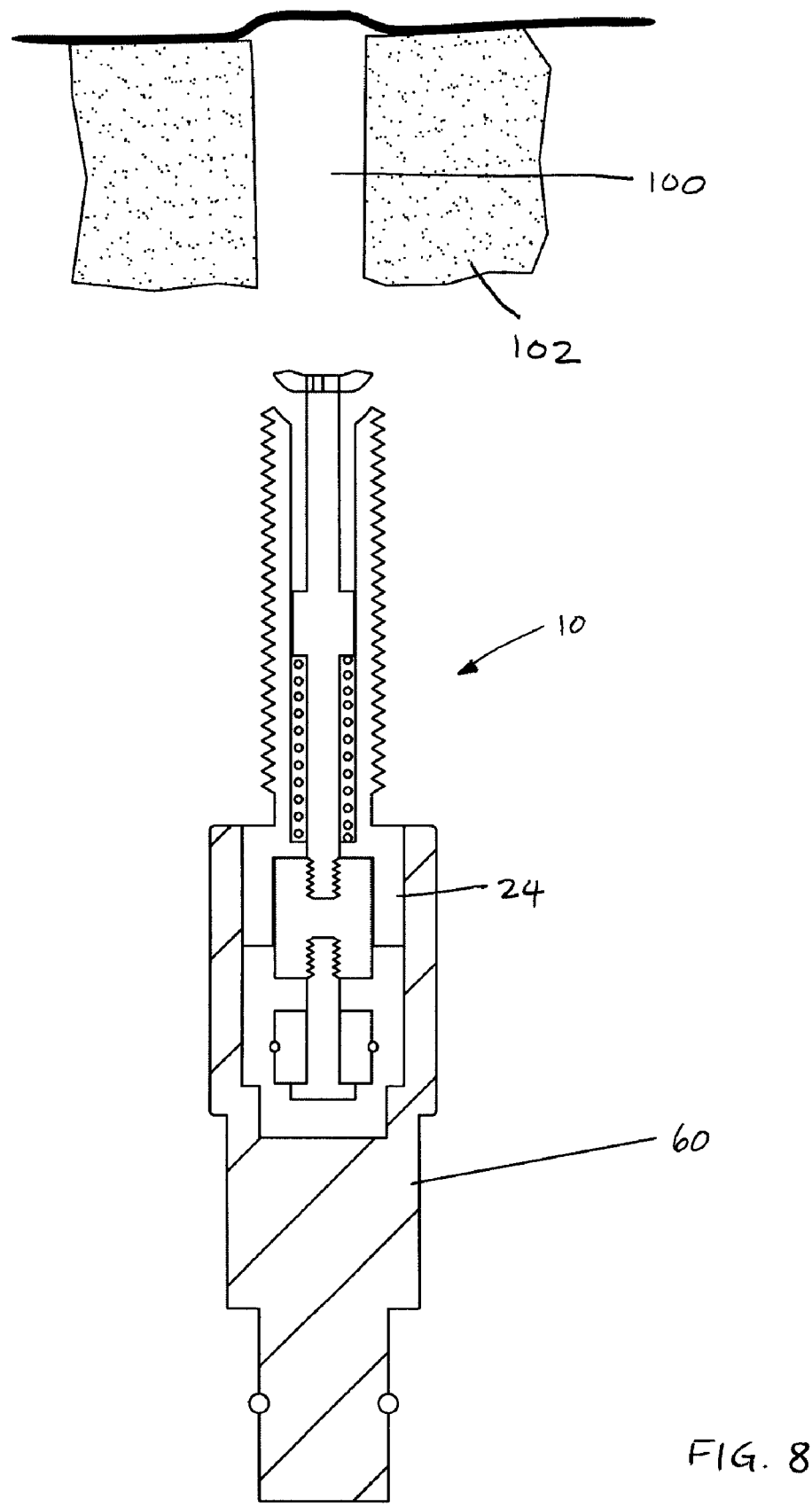
FIG. 8 is a longitudinal section view of a system of the bone cutter device of FIG. 1 engaged by the second tool for removal from the hole in the maxillary bone.

Referring to FIG. 8, the device 10 is then removed from the hole 100 in the maxillary bone 102 by re-engaging the larger socket 60 at the third tool engagement structure 24 and rotating the tubular element 24 to unthread it from the bone.

More particularly, in operation, the gingiva is opened to reveal the underlying maxillary bone at the location of an intended dental implant. A hole is preferably marked in the bone at the location with a dental burr, a small pilot hole is preferably drilled in the bone to within preferably approximately 1 to 2 mm of the subantral membrane, and a preferably 3.2 mm drill bit (or drill, used interchangeably) is used to enlarge the hole to such diameter also to within preferably approximately 1 to 2 mm of the subantral membrane. A 3.2 mm drill bit is preferred, as it corresponds with the tap dimension, is suitable for curette passage (as described below), and approximates the dimension of an anchor of a dental implant at the conclusion of the procedure. The device is then advanced within the drilled hole by coupling a ratchet socket 60 over the third tool engagement structure 24 and advancing the cutting element within the hole. During initial insertion, it is appreciated that the cutting element is unloaded. Once the cutting element reaches the end of the drilled hole, the cutting element is forced against the tap, moved against the bias of the spring, and enters a loaded configuration. Socket 60 is removed from over engagement structure 24, and a different smaller socket 68 having an opening sized and shaped for rotational engagement of the first and second tool engagement structures 20, 22 is coupled to the device. Torque is applied to the device using the smaller socket tool to rotate the cutting element until the cutting element reaches the subantral membrane and, under force of the spring, displaces relative to the distal end of the tap and lifts the subantral membrane off the maxillary bone. The smaller socket is removed from the device, and the larger socket 60 is re-attached and used to remove the device from the hole.

After the hole is cut through the maxillary bone, any suitable instrument(s) and technique(s) then can be used to separate and lift the subantral membrane from the floor of the maxillary sinus to define a space for receiving bone graft material that can support an implant. In a preferred embodiment, curettes as described in previously incorporated U.S. Ser. No. 11/669,449 are used to separate the subantral membrane from the maxillary sinus floor. Once the subantral membrane is separated from the floor of the sinus, a bone packer is used to place and compact bone graft material under the lifted subantral membrane. At this time, the gingiva may be closed for a period of healing. Alternatively, a drill corresponding to the anchor of the intened implant is used to drill a hole of corresponding diameter, the implant is placed therein, and the gingiva is closed thereover.

It is also appreciated that the above described cutter device 10 can be fully operated with two sockets that differently engage the first and second tool engagement structures 20, 22.

Figure 6:
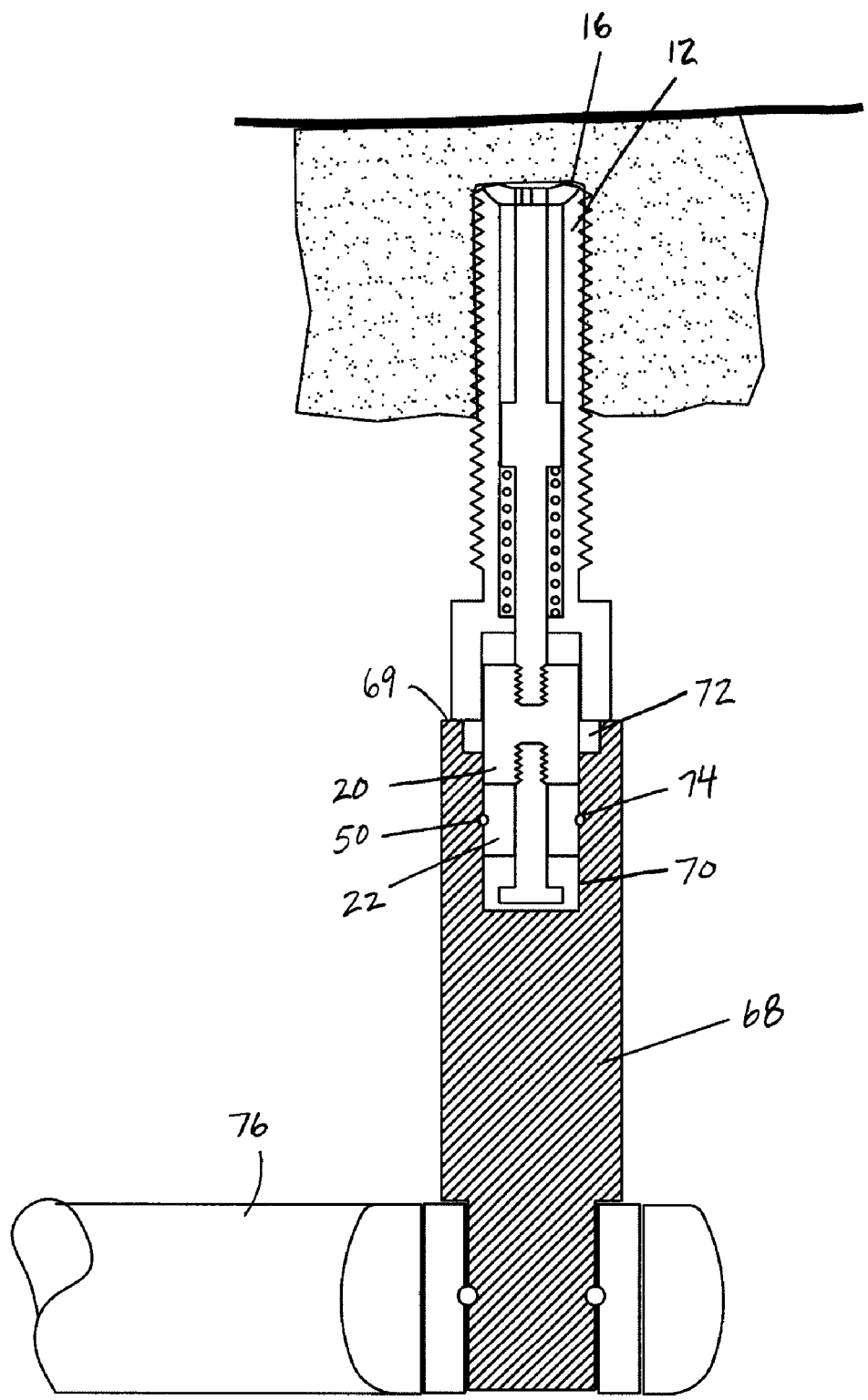
FIG. 6 is a longitudinal section view of a system of the bone cutter device of FIG. 1 engaged by a first tool for bone cutting and advancement into a hole in the maxillary bone, with the device in a loaded configuration.
Figure 9:
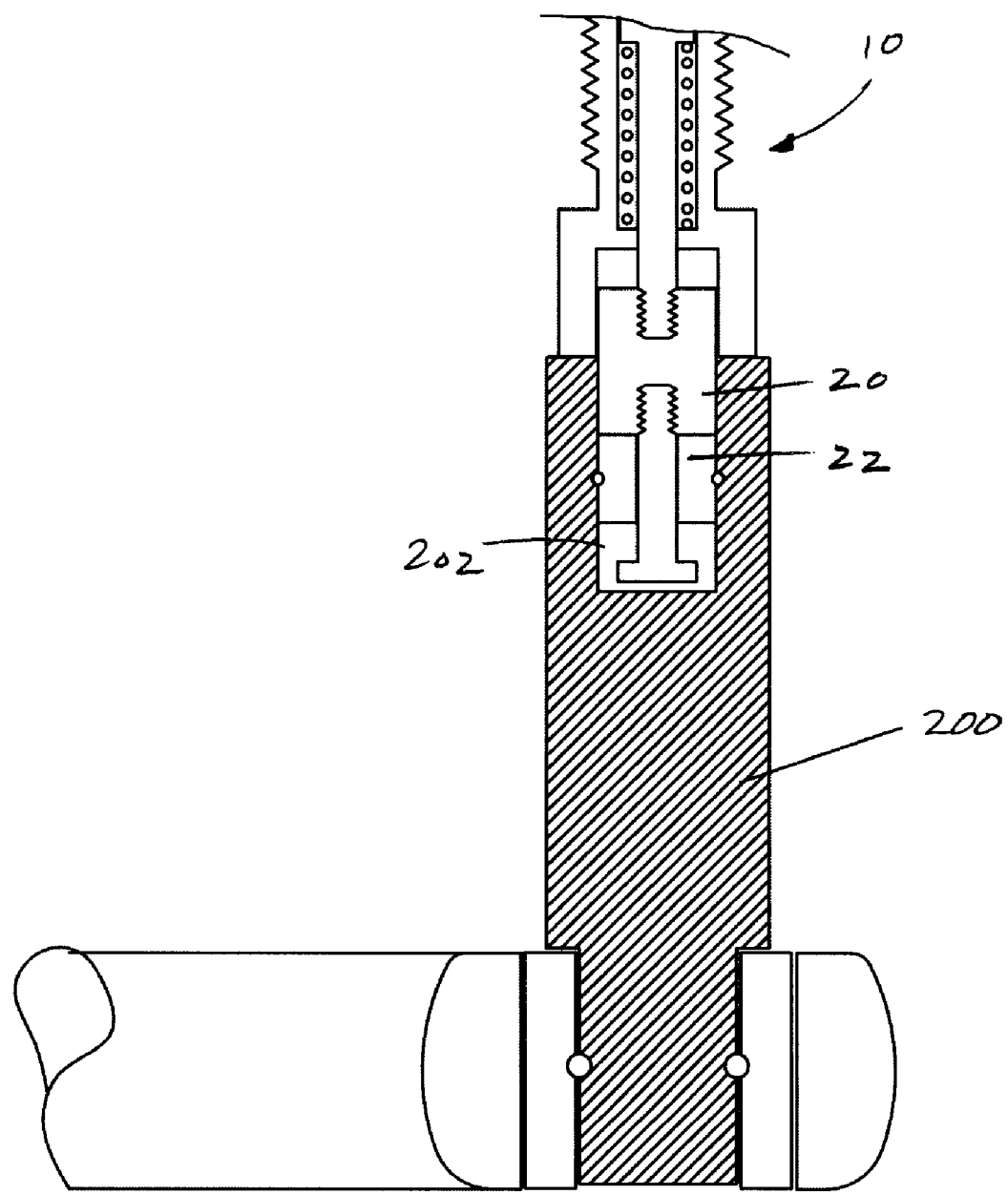
FIG. 9 is a broken longitudinal section view of a system of the bone cutter device of FIG. 1 engaged by another tool, according to an alternate embodiment of the invention.

Referring to FIG. 9, socket 200 includes an opening 202 that rotationally engages both first and second engagement structures 20, 22 in the unloaded configuration. Such socket 200 rotationally advanced the device 10 when the cutting element is in the unloaded configuration. The second socket 68 is as shown and functions in cooperation with the device as described with respect to FIGS. 6 and 7. Such sockets 68, 200 can also be provided in several lengths.

Turning now to FIGS. 10 through 14, a second embodiment of a cutting device 310 is shown. Cutting device 310 generally includes a tap 312 and a tap body 314 into which the tap 312 is fixed. The tap body 314 extends radially outward relative to said tap 312 to provide substantial surface area for manual rotation and includes an axial bore 316, an outer surface 318 treated to facilitate manual rotation, e.g., knurled, and a distal taper 320 to enhance visualization of the cutting site. The tap 312 includes distal cutting flutes 322 and self-tapping threads 324. The proximal end of the tap 312 includes a barrel 326 that is provided with longitudinal ridges 327 and preferably interference fit into the distal end of the bore 316 of the tap body 314. The barrel 326 may also be fixed into the tap body 314 via bonding or other means. A flange 328 operates as a stop to seat the tap 312 within the tap body 314 and the prevents travel of tap into the tap body when under load.

A cutter 330 is situated at the distal end of the tap 312. The outer diameter of the cutter 330 is slightly smaller than the outer diameter of the tap 312. The cutter 330 preferably includes three cutting blades 331a, 331b, 331c structurally adapted to remove maxillary bone. The blades of the cutter 330 are angled so that the cutter is slightly "dished" to cut at the circumferential edges first, similar to a hole saw. This enables the cutter to cut a disc of bone, as discussed below, and helps prevent the radial edges of the blades from contacting the subantral membrane. The cutter 330 is fixed to a piston 332 that extends through an axial bore 333 in the tap 312 and is then rotatably fixed to and extends through a first toothed gear 334. The first toothed gear 334 includes teeth 336 that are directed in the proximal direction and are preferably angled at approximately 45°. The first toothed gear 334 and the proximal end of the tap 312 are rotatably fixed relative to one another, e.g., via two interfering tubular sections 337a, 337b or via a spline engagement, but longitudinally displaceable relative to each other (compare FIGS. 13 and 14).

The device 310 also includes a drive shaft 338 including a second toothed gear 340 including teeth 342 directed distally to mate with the teeth 336 of the first toothed gear 334. The drive shaft 338 also preferably includes a proximal end 344 with a non-circular cross section for rotational fixation with a driver knob 346. The driver knob 346 includes a non-circular bore 347 for receiving the proximal end 344 of the drive shaft 338, an indicator hole 348 (described below), external ridges 350 to facilitate manual rotation thereof, and preferably a curved proximal surface 352 to comfortably seat against a portion of the hand of a user.

A spring 354 is preferably provided between the first and second toothed gears 334, 340 to bias the gears apart into a unengaged configuration when the device 310 is unloaded. Referring to FIG. 14, when the cutter 330 is forced against bone to provide the device in a loaded configuration, the first toothed gear 334 is moved against the bias of the spring 354 to engage the first and second gears 334, 340 relative to each other. This also causes the proximal end of the piston 332 to extend through the indicator hole 348 to indicate to the user that bone is being cut. It is also appreciated that the device may be constructed without the spring, utilizing, e.g., the angle of teeth on gears 334, 340 to apply a relative force between the piston 332 (and cutter 330) and the tap 312.

Referring to FIG. 13, when the gears are disengaged, e.g., because the cutter 330 has pierced all maxillary bone and the spring 354 has caused the cutter 330 to lift the subantral membrane, the proximal end of the piston 332 is substantially flush with the proximal surface 352 of the driver knob 346 at the indicator hole 348 and indicates to the user that the cutting process is complete.

In operation of the second embodiment of the cutter device, the user advances the tap 312 into a pilot hole in bone by manual rotation of the tap body 314 (which is rotatably fixed relative to the tap 312). During initial insertion, it is appreciated that the cutter 330 is unloaded and the drive gears 334, 340 are disengaged. Once the cutter 330 at the distal end of the tap 312 reaches the end of the pilot hole, the cutter 330 is forced against the distal end of the tap 314, and the first drive gear 334 is longitudinally moved against the bias of the spring 354 to engage the second drive gear 340. This is visually indicated to the user by the movement of the proximal end of the piston 332 through the indicator hole 348 on the driver knob 346 (which appears to the user as a raised button on the knob). As the gears 334, 340 are now engaged, user rotation of the driver knob 346 causes rotation of the drive shaft 338 which rotates the second gear 340 which is rotationally engaged to the first gear 334. As the first gear 334 is then rotated, the tap 312 and cutter 330 are together rotated to effect cutting of bone. Once the bone has been cut through, the spring 354 operates to move the first and second drive gears 334, 340 apart which results in cutter 330 displacement relative to the distal end of the tap 312 and lifting of the subantral membrane off the maxillary bone. In addition, the proximal end of the piston 332 is then retracted into the driver knob 346 to provide a visual indication to the user that the bone has been cut through and that the drive gears 334, 340 are disengaged.

It is appreciated that the first gear 334 may be partially or completely rotationally disengaged from the proximal end of the tap 312; i.e., that there may be limited or no rotational fixation therebetween. If the first drive 334 and tap 312 are partially disengaged, e.g., 90°-180° of rotation is permitted therebetween (but not 360°) then the knob 346 may be used to rotate the cutter 330 in a twisting manner to remove bone, and when sufficient bone has been removed the tap 312 can be advanced by rotation of the tap body 314. If the first gear 334 is completely disengaged from the tap 312 (such that at least 360° of rotation is permitted) then the knob 346 may be used to reciprocate or rotate the cutter 330 to remove bone, and when sufficient bone has been removed the tap 312 can be advanced further into the bone by rotation of the tap body 314.

Once the maxillary bone is broken through, the cutter device is removed, appropriate tools are used to detach a portion of the subantral membrane from the maxillary bone, and bone graft material is placed into the hole and under the lifted subantral membrane.

After the hole is cut through the maxillary bone, any suitable instrument(s) and technique(s) then can be used to separate and lift the subantral membrane from the floor of the maxillary sinus to define a space for receiving bone graft material that can support an implant. In a preferred embodiment, curettes as described in previously incorporated U.S. Ser. No. 11/669,449 are used to separate the subantral membrane from the maxillary sinus floor. Once the subantral membrane is separated from the floor of the sinus, a bone packer is used to place and compact bone graft material under the lifted subantral membrane. At this time, the gingiva may be closed for a period of healing. Alternatively, a drill corresponding to the anchor of the intened implant is used to drill a hole of corresponding diameter, the implant is placed therein, and the gingiva is closed thereover.

Figure 15:
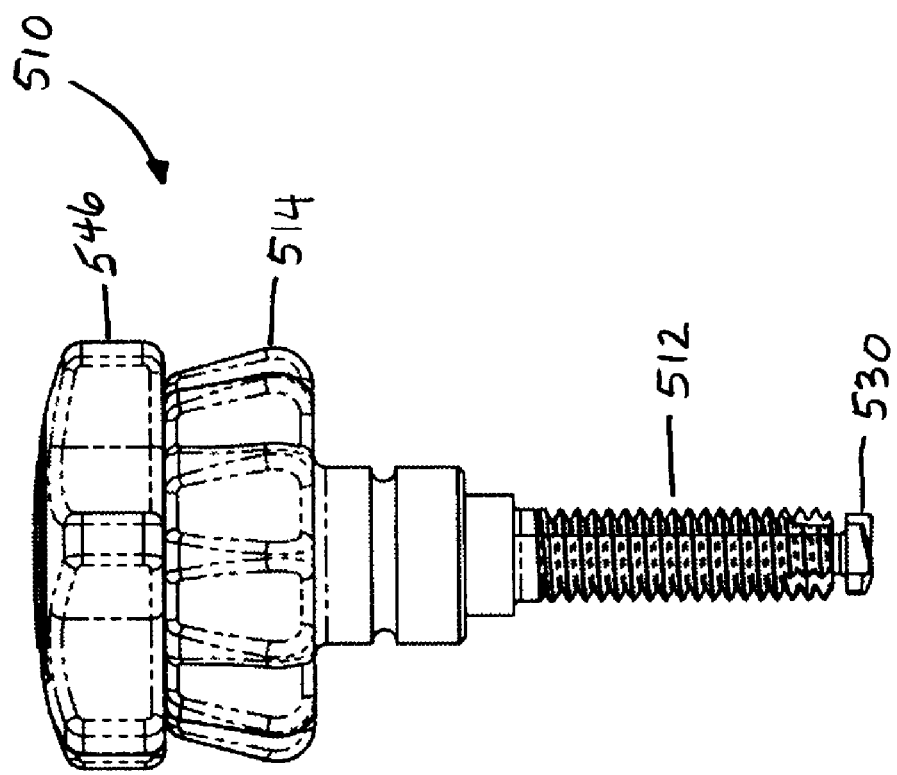
FIG. 15 is a longitudinal view of another embodiment of a bone cutter device according to the invention shown in an unloaded configuration.

Turning now to FIGS. 15 through 17, a third embodiment of a cutting device 510, substantially similar to cutting device 3 10. Cutting device 510 is substantially similar to cutting device 310, with like parts having reference numerals incremented by 200. Cutting device 510 generally include a tap 512 and a tap body 514 into which the tap 512 is fixed. The tap body 514 extends radially outward relative to the tap 512 to provide substantial surface area and ergonomics for manual rotation. The tap body 514 includes an axial bore 516 and external gripping ridges 518. The tap 512 includes distal cutting flutes 522 and self-tapping threads 524. The proximal end of the tap 512 includes a barrel 526 that is provided with longitudinal ridges 527 and is preferably interference fit into the distal end of the bore 516 of the tap body 514. The barrel 526 may also be fixed into the tap body 514 via bonding or other means. A flange 528 operates as a stop to seat the tap 512 within the tap body 514 and the prevents travel of tap into the tap body when under load.

A cutter 530 is situated at the distal end of the tap 512. The outer diameter of the cutter 530 is slightly smaller than the outer diameter of the tap 512. The cutter 530 preferably includes three cutting blades 531a, 531b, 531c structurally adapted to remove maxillary bone. The cutter 530 is preferably slightly concave to allow the outer edges of the blades of the cutter to operate to remove the bone material. The cutter 530 is fixed to a piston 532 that extends through an axial bore 533 in the tap 512 and extends through a first toothed gear 534. The piston 532 is rotatably fixed relative to the first tooth gear 534 via a hex engagement at 535a, 535b when the cutter is forced against the bone. The first toothed gear 534 includes two teeth 536 (one shown) that are directed in the proximal direction and are preferably angled at approximately 90°. The first toothed gear 534 and the proximal end of the tap 512 are rotatably fixed relative to one another, e.g., via two interfering tubular sections 537a, 537b or via a spline engagement, but longitudinally displaceable relative to each other. A retaining ring 539 seats in a groove 533 on the piston 532 of the cutter 530 and retains the tap 512, cutter 530, and first toothed gear 534 in a tap assembly 541.

The device 510 also includes a drive shaft 538 including a second toothed gear 540 including two teeth 542 directed distally to mate with the teeth 536 of the first toothed gear 534. The drive shaft 538 also preferably includes a proximal end 544 with a non-circular cross section for press-fit engagement within a bore 547 in a driver knob 546. The driver knob includes external ridges 550 to facilitate manual rotation thereof, and preferably a curved proximal surface 552 to comfortably seat against a portion of the hand of a user.

A spring 554 is provided between the first and second toothed gears 534, 540 to bias the gears apart into a unengaged configuration when the device 510 is unloaded. When the cutter 530 is forced against bone to provide the device in a loaded configuration, the first toothed gear 534 is moved against the bias of the spring 554 to engage the first and second gears 534, 540 relative to each other. When the cutter 530 has pierced all maxillary bone, the spring 554 causes the cutter 530 to lift the subantral membrane, and the gears 534, 540 are disengaged.

The third embodiment of the cutter device 510 is used in substantially the same manner as the second embodiment of the cutter device 310.

All components of the several embodiments of the cutting device are preferably made of metal or metal alloy and/or one or more suitable hard polymeric materials or ceramic. It is especially preferable that the cutting element be made of metal, metal alloy or ceramic, or coated with a ceramic.

Figure 18:
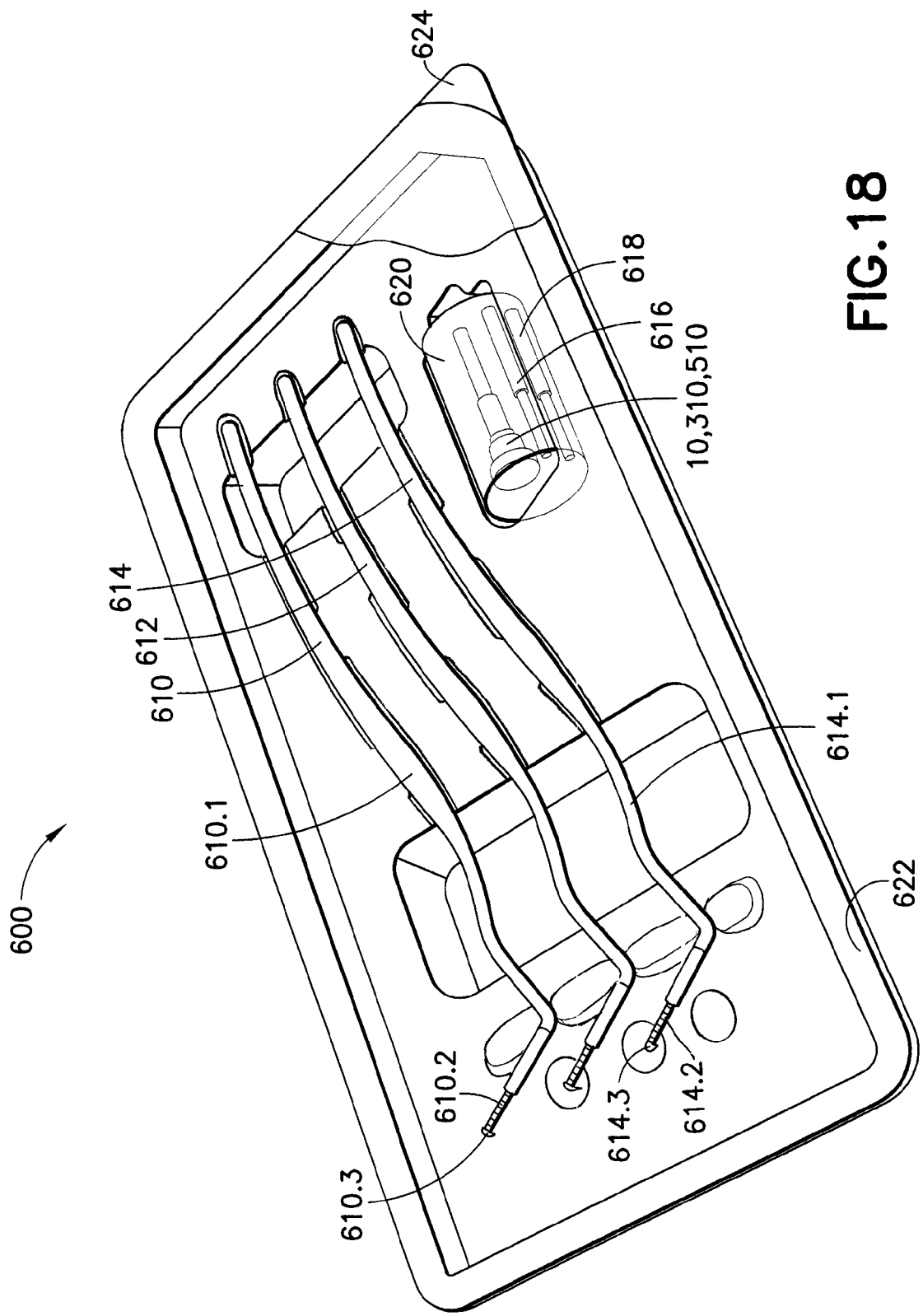
FIG. 18 is a perspective view of a surgical tray kit including instruments for performing a sinus elevation procedure according to the invention.

Referring to FIG. 18, in accord with another aspect of the invention, a collection of tools required to perform the procedure are provided together as a kit 600 in sterilized form. The kit 600 of tools include at least the cutting device 10, 310, 510 of the invention as well as one or more curettes 610, 612. The tools preferably include two curettes each of a different dimension such that the curettes are adapted to separate a different extent of the subantral membrane surrounding the hole defined in the maxillary bone by the cutter. As described in more detail in previously incorporated U.S. Ser. No. 11/669,449, curette 610 includes a handle 610.1, a support structure 610.2 extending therefrom, and a thin member 610.3 extending from the distal end of the support structure and preferably rotatable relative to the handle 610.1. The thin member 610.3 defines a blade-like portion for dissecting the subantral membrane from the floor of the maxillary sinus. The support structure 610.2 and thin member 610.3 are sized to be inserted through the hole cut by the cutter device, with curettes of larger gauge having thin members of sufficient flexibility and resiliency to flex during insertion through the hole. The leading end of the thin member 610.3 is sufficiently soft to prevent rupture of the subantral membrane. The kit 600 of tools preferably also includes a bone packer 614 adapted to push and pack bone graft material into a drilled hole. The bone packer 614 includes a handle 614.1, a mounting structure 614.2 extending perpendicularly relative to the handle, and a blunt cylinder 614.3 mounted at the end of the mounting structure and having a diameter of less than 3.2 mm. The cutting device 10, 310, 510 is preferably in a separately sealed packaged 620 within the kit 600. Kit 600, and package 620, preferably also include a pilot drill 616 as well as a 3.2 mm drill 618 for use during the above-described procedure. All tools provided are presented in a tray 622, sealed with a preferably peel-away cover 624, and in sterilized condition ready for use.

While the cutter device has been described with respect to performing bone removal on the maxillary bone, it is appreciated that the device may have utility in other surgical procedures. For example, the device may be used to manually cut a bone in cranial procedures for access to the space within the cranium, e.g., for nerolosurgical procedures. In addition, the device may be used for spinal procedures to access the space within the spinal column. Furthermore, the device may be used for otological procedures to access the middle ear for ossicular repair or for ossicular prosthesis implantation. For the various procedures, it is appreciated that the device may be provided in dimensions suitable for the respective procedures.

There have been described and illustrated herein embodiments of a bone cuter device, a system including the device and tools for use therewith, and a method of using the same. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A bone cutter device, the device comprising:
    a) a tubular element including a distal tap having a threaded exterior surface configured to be advanced into a hole in bone, said tubular element including a proximal end, a distal end, and an axial bore;

b) a piston longitudinally displaceable within said axial bore and having a distal end;

c) a cutting element mounted on said distal end of said piston adjacent said distal end of said tap, said cutting element forced away from said distal end of said tubular element by a spring force of a spring and displaceable against said spring force when under load to be located in contact with said distal end of said tap;

d) a first drive means rotationally fixed at a proximal end of said tubular element for rotationally advancing said tap; and e) a second drive means for rotating said cutting element when said cutting element is under load.

2. A bone cutter device according to claim 1, wherein:
said first drive means includes a first manual drive body.

3. A bone cutter device according to claim 2, wherein:
said second drive means includes first and second gears engageable when said cutting element is under load, wherein under load said first gear is rotationally fixed to said cutting element and said second gear is rotationally fixed to a second manual drive body.

4. A bone cutter device according to claim 3, wherein:
said first and second gears include engageable teeth formed at 90° angles.

5. A bone cutter device according to claim 3, wherein:
said first and second gears include engageable teeth formed at 45° angles.

6. A kit for a sinus elevation procedure in bone, comprising:
a) a bone cutter device including
   i) a tubular element including a distal tap having a threaded exterior surface configured to be advanced into a hole in bone, said tubular element including a proximal end, a distal end, and an axial bore,
   ii) a piston longitudinally displaceable within said axial bore and having a distal end,
   iii) a cutting element mounted on said distal end of said piston adjacent said distal end of said tap, said cutting element forceable away from said distal end of said shaft by a spring force of a spring and displaceable against said spring force when under load to be located in contact with said distal end of said tap,
   iv) a first drive means rotationally fixed at a proximal end of said tubular element for rotationally advancing said tap, and
   v) a second drive means for rotating said cutting element when said cutting element is under load;
b) at least one separating means for separating the subantral membrane from the maxillary sinus bone; and
c) a container including the bone cutter device and the separating means.

7. A kit according to claim 6, wherein:
said bone cutter device is manually operable.

8. A kit according to claim 7, wherein:
said bone cutter device includes a first knob for advancing the device within the closed-end hole, and a second knob for rotating the cutter element.

9. A kit according to claim 6, wherein:
said separating means including a handle, a mounting structure extending at an angle from the handle, and a dissecting member tapering in thickness toward a free end for dissecting the subantral membrane from the maxillary bone.

10. A kit according to claim 9, wherein:
said kit includes two separating means, each separating means including a dissecting member having at least one of distinct dimension and flexibility.

11. A kit according to claim 6, further comprising:
a bone packer including a handle, a mounting structure extending perpendicularly relative to the handle, and a blunt cylinder mounted at the end of the mounting structure and having a diameter not exceeding 3.2 mm.

12. A kit according to claim 6, further comprising:
at least one bone drill.

13. A kit according to claim 12, wherein:
said at least one drill includes a pilot drill and a 3.2 mm drill.

14. A kit according to claim 6, wherein:
said container comprises a sealed tray.

15. A kit according to claim 6, wherein:
said container and the contents therein are sterilized.

16. A kit for a sinus elevation procedure, comprising:
a) a bone cutter device including
   i) a tubular element including a distal tap having a threaded exterior surface configured to be advanced into a hole in bone, said tubular element including a proximal end, a distal end, and an axial bore,
   ii) a piston longitudinally displaceable within said axial bore and having a distal end,
   iii) a cutting element mounted on said distal end of said piston adjacent said distal end of said tap, said cutting element forceable away from said distal end of said shaft by a spring force of a spring and displaceable against said spring force when under load to be located in contact with said distal end of said tap,
   iv) a first drive means rotationally fixed at a proximal end of said tubular element for rotationally advancing said tap, and
   v) a second drive means for rotating said cutting element when said cutting element is under load;
b) a plurality of separating means for separating the subantral membrane from the maxillary sinus bone, each said separating means including a dissecting member having at least one of distinct dimension and flexibility;
c) a bone packer including a handle, a mounting structure extending perpendicularly relative to the handle, and a blunt cylinder mounted at the end of the mounting structure and having a diameter not exceeding 3.2 mm;
d) at least one bone drill; and
e) a container including the bone cutter device, said plurality of separating means, said bone packer and said at least one bone drill.

17. A kit according to claim 16, wherein:
said at least one drill includes a pilot drill and a 3.2 mm drill.

18. A kit according to claim 16, wherein:
said container comprises a sealed tray.

19. A kit according to claim 16, wherein:
said container and the contents therein are sterilized.

20. A method of drilling in bone, comprising:
a) forming an initial hole in bone that does not extend completely through the bone;
b) inserting a bone cutting device into the initial hole, said bone cutting device including
   i) a tubular element including a distal tap having a threaded exterior surface configured to be advanced into a hole in bone, said tubular element including a proximal end, a distal end, and an axial bore,
   ii) a piston longitudinally displaceable within said axial bore and having a distal end,
   iii) a cutting element mounted on said distal end of said piston adjacent said distal end of said tap, said cutting element forceable away from said distal end of said tubular element by a spring force of a spring and displaceable against said spring force when under load to be located in contact with said distal end of said tap,
  iv) a first drive means rotationally fixed at a proximal end of said tubular element for rotationally advancing said tap, and
  v) a second drive means for rotating said cutting element when said cutting element is under load;
c) cutting bone by rotating said cutting element of the bone cutting device with the second drive means applying torque to the cutting element; and
d) automatically disengaging the torque force from the second drive means to the cutting element when the cutting element breaks through the bone to define a throughhole.

21. A method according to claim 20, wherein:
said forming an initial hole is formed in the maxillary bone, and
when the cutting element breaks through the bone to define a throughhole, the cutting element reaches the subantral membrane.

22. A method according to claim 21, further comprising:
removing the cutting device from the throughhole;
separating a portion of the subantral membrane from the floor of the maxillary sinus to define a space for receiving bone graft material; and
placing bone graft material into said space.

23. A method according to claim 22, further comprising:
implanting a dental implant into the maxillary bone at the location of where the bone graft material was placed.

24. A method according to claim 20, wherein:
said automatically disengaging removes the torque to any rotationally fixed portion of the cutting device.

25. A method of performing a sinus elevation, comprising:
a) drilling the maxillary bone to within approximately 2 mm of the sinus membrane to form a closed-end hole;
b) advancing a bone cutter device into the closed-end hole in the maxillary bone below the sinus membrane, the bone cutter device including
  i) a tubular element including a distal tap having a threaded exterior surface configured to be advanced into a hole in bone, said tubular element including a proximal end, a distal end, and an axial bore,
  ii) a piston longitudinally displaceable within said axial bore and having a distal end,
  iii) a cutting element mounted on said distal end of said piston adjacent said distal end of said tap, said cutting element forceable away from said distal end of said tubular element by a spring force of a spring and displaceable against said spring force when under load to be located in contact with said distal end of said tap,
  iv) a first drive means rotationally fixed at a proximal end of said tubular element for rotationally advancing said tap, and
  v) a second drive means for rotating said cutting element when said cutting element is under load;
c) operating the bone cutter device to break through the maxillary bone and reach the sinus membrane to define a through-hole in the bone under the sinus membrane;
d) removing the bone cutter device from the bone;
e) inserting a first dissecting tool through the through-hole to dissect a portion of the sinus membrane from the maxillary bone and raise the sinus membrane relative to the maxillary bone;
f) packing bone under the raised sinus membrane.

26. A method according to claim 25, further comprising:
g) drilling a hole through the bone packed under the raised sinus membrane;
h) implanting a dental implant through the drilled hole.

27. A method according to claim 25, further comprising:
after inserting a first dissecting tool, inserting a second dissecting tool between the sinus membrane and maxillary bone, said second dissecting tool having at least one of a different dimension and flexibility relative to said first dissecting tool.

28. A method according to claim 27, wherein:
said drilling maxillary bone drills the maxillary bone with a 3.2 mm drill bit.

29. A method according to claim 28, wherein:
said drilling the maxillary bone drills the maxillary bone with a pilot drill prior to drilling with the 3.2 mm drill bit.

30. A bone cutter device, the device comprising:
a) a tubular element including a distal tap having a threaded exterior surface configured to be advanced into a hole in bone, said tubular element including a proximal end, a distal end, and an axial bore;
b) a piston longitudinally displaceable within said axial bore and having a distal end;
c) a cutting element including at least one blade mounted on said distal end of said piston adjacent said distal end of said tap, said cutting element biased away from said distal end of said tubular element by a first distance when said cutting element is unloaded, and said cutting element displaceable against said bias to be closer to said distal end of said tap when under load;
d) a first drive means rotationally fixed at a proximal end of said tubular element for rotationally advancing said tap; and
e) a second drive means for rotating said cutting element when said cutting element is under load.

31. A bone cutter device according to claim 30, wherein:
a spring provides said bias to said cutting element.

32. A bone cutter device according to claim 30, wherein:
said first drive means includes a first manual drive body.

33. A bone cutter device according to claim 32, wherein:
said first manual drive body comprises a driver knob with external ridges for engagement by fingers of a hand of a user.

34. A bone cutter device according to claim 33, wherein:
said driver knob has a curved proximal surface that comfortably seats against a portion of the hand of the user.

35. A bone cutter device according to claim 32, wherein:
said second drive means includes first and second gears that are engaged when said cutting element is sufficiently loaded to move said cutting element against said bias and disengaged when said cutting element is unloaded,
wherein when said cutting element is loaded, said first gear is fixed relative to said cutting element and said second gear is fixed relative to a second manual drive body.

36. A bone cutter device according to claim 35, wherein:
said first and second gears include engageable teeth formed at 90° angles.

37. A bone cutter device according to claim 35, wherein:
said first and second gears include engageable teeth formed at 45° angles.

38. A bone cutter device according to claim 30, wherein:
said cutting element includes three and no more than three cutting blades.

39. A bone cutter device, the device comprising:
a) a tubular element including a distal tap having a threaded exterior surface configured to be advanced into a hole in bone, said tubular element including a proximal end, a distal end, and an axial bore;

b) a piston longitudinally displaceable within said axial bore and having a distal end;

c) a cutting element mounted on said distal end of said piston adjacent said distal end of said tap, said cutting element forced away from said distal end of said tubular element by a force and displaceable against said force when under load to be located in contact with said distal end of said tap;

d) a first drive means rotationally fixed at a proximal end of said tubular element for rotationally advancing said tap, said first drive means including a first manual drive body; and e) a second drive means for rotating said cutting element when said cutting element is under load, said second drive means including first and second gears engageable when said cutting element is under load, wherein under load said first gear is rotationally fixed to said cutting element and said second gear is rotationally fixed to a second manual drive body.

40. A bone cutter device according to claim 39, wherein: said first and second gears include engageable teeth formed at 90° angles.

41. A bone cutter device according to claim 39, wherein: said first and second gears include engageable teeth formed at 45° angles.

42. A bone cutter device according to claim 1, wherein: said first drive means includes a first tool engageable element.

43. A bone cutter device according to claim 42, wherein: said second drive means includes a second tool engageable element proximally displaced relative to and smaller in diameter than said first tool engageable element.

* * * * *